United States Patent
Zhang

[11] Patent Number: 6,105,366
[45] Date of Patent: Aug. 22, 2000

[54] METHOD FOR MONITORING THE EMISSION CONTROL SYSTEM OF A SPARK IGNITION INTERNAL COMBUSTION ENGINE

[75] Inventor: Hong Zhang, Regensburg, Germany

[73] Assignee: Siemens Aktiengesellschaft, Munich, Germany

[21] Appl. No.: 09/201,732

[22] Filed: Nov. 30, 1998

[30] Foreign Application Priority Data

Nov. 28, 1997 [DE] Germany ............ 197 52 965

[51] Int. Cl.$^7$ ........................ F01N 3/00
[52] U.S. Cl. .............. 60/274; 60/276; 60/277; 60/285; 123/688; 123/703
[58] Field of Search ............ 60/274, 285, 276, 60/277; 123/688, 703

[56] References Cited

U.S. PATENT DOCUMENTS

| | | | |
|---|---|---|---|
| 5,117,631 | 6/1992 | Moser | 60/274 |
| 5,214,915 | 6/1993 | Schneider et al. | 60/274 |
| 5,673,555 | 10/1997 | Achleitner | 60/274 |
| 5,836,153 | 11/1998 | Staufenberg et al. | 60/274 |
| 5,862,661 | 1/1999 | Zhang et al. | 60/274 |

FOREIGN PATENT DOCUMENTS

| | | |
|---|---|---|
| 41 12 480 A1 | 10/1992 | Germany . |
| 42 33 977 A1 | 4/1993 | Germany . |
| 43 28 099 A1 | 3/1994 | Germany . |
| 43 38 342 A1 | 5/1995 | Germany . |
| 196 45 279 A1 | 5/1997 | Germany . |
| 195 45 693 A1 | 6/1997 | Germany . |
| 196 23 335 C1 | 8/1997 | Germany . |
| 197 11 295 A1 | 10/1997 | Germany . |

*Primary Examiner*—Thomas Denion
*Assistant Examiner*—Thai-Ba Trieu
*Attorney, Agent, or Firm*—Herbert L. Lerner; Laurence A. Greenberg; Werner H. Stemer

[57] ABSTRACT

An emission control system is monitored by measuring time periods during which the signal of a post-catalyst lambda probe lies below or above an engine speed/load dependent threshold value. The measurements are weighted with an engine speed/load dependent value and subsequently summed so that a total reference time period, which constitutes a measure of the additionally emitted pollutants, can be related to the overall operating time period. If the ratio exceeds a predefined value, a faulty function of the pre-catalyst lambda probe is diagnosed. The method permits the onboard diagnosis of the lambda control of the catalytic emission treatment system.

10 Claims, 2 Drawing Sheets

METHOD FOR MONITORING THE EMISSION CONTROL SYSTEM OF A SPARK IGNITION INTERNAL COMBUSTION ENGINE

BACKGROUND OF THE INVENTION

Field of the Invention

The invention lies in the automotive field. More specifically, the invention relates to a method for monitoring the emission control system of a spark ignition internal combustion engine provided with a lambda-controlled catalytic converter. A so-called pre-catalyst lambda probe is arranged upstream of the catalytic converter in the exhaust gas flow direction, and a post-catalyst lambda probe is arranged downstream of the catalytic converter. The fuel supply system of the internal combustion engine is controlled by master control of the post-catalyst lambda probe in such a way that the signal of the pre-catalyst lambda-probe performs an oscillation about the value lambda $\lambda=1$.

In an emission control system having two lambda probes, a pre-catalyst lambda probe (also referred to as a pre-cat lambda sensor) is used upstream of the catalytic converter as a measuring probe. A post-catalyst lambda probe (also referred to as a post-cat lambda sensor) is used downstream of the catalytic converter as a monitor probe for monitoring and compensating a static or dynamic lambda shift of the pre-catalyst lambda probe signal which would lead to an increase in emissions. Usually, the two lambda probes have two step action and their emitted voltage signal is, as in all lambda probes, dependent on the residual oxygen contained in the emissions. The oxygen content in the emissions depends in turn on the air-fuel mixture which has been fed to the internal combustion engine. In the case of a leaner mixture ($\lambda>1$), the output voltage of the lambda probe is usually below 100 mV, but in the region of range $\lambda=1$ it changes virtually instantaneously and extends beyond 0.9 V in the case of a rich mixture ($\lambda<1$). This effect is referred to as two step action.

The dynamic and static properties of the pre-catalyst lambda probe are changed as a result of aging of the probe and contamination. As a result, the control point of the lambda control is shifted. For example, contamination with phosphorous can lead to an asymmetrical change in the probe response time and thus to a shifting of the probe control in the lean direction outside the optimum lambda range for the catalytic conversion. As a result, for example, the $NO_x$ emission may rise beyond a permitted limit. The post-catalyst lambda probe is used as a monitor probe for monitoring the catalytic conversion and for the fine control of the mixture so that the lambda value which is most favorable for the conversion can always be maintained. This is referred to as master control.

However, a functional diagnosis of the pre-catalyst lambda probe is possible only to a limited degree with the prior art. In particular, it is not possible to determine for how long the optimum lambda range has not been maintained, and how large an associated increase in emissions is.

SUMMARY OF THE INVENTION

It is accordingly an object of the invention to provide a method for monitoring the emission control system of an internal combustion engine with lambda-controlled catalytic emission treatment, which overcomes the above-mentioned disadvantages of the heretofore-known devices and methods of this general type and which permits faulty lambda probes to be diagnosed.

With the foregoing and other objects in view there is provided, in accordance with the invention, a method for monitoring an emission control system of a spark ignition internal combustion engine, wherein the emission control system includes a lambda-controlled catalytic converter subjected to an exhaust gas flow, a pre-catalyst lambda probe disposed upstream of the catalytic converter in an exhaust gas flow direction, and a post-catalyst lambda probe disposed downstream of the catalytic converter. The method comprises the following steps:

controlling a fuel supply system of an internal combustion engine by master control of the post-catalyst lambda probe such that a signal of the pre-catalyst lambda-probe oscillates about a value $\lambda=1$;

measuring a first time period in which a signal of the post-catalyst lambda probe lies below a predefined lower threshold value and a second time period in which the signal of the post-catalyst lambda probe lies above a predefined upper threshold value, and weighting the first and second time periods with respect to an upward transgression of a permitted emission of pollutants to form two reference time periods in dependence on rotational speed and a load;

adding the reference time periods to form a total reference time period; and diagnosing a fault in the pre-catalyst lambda probe if the total reference time period exceeds a predefined portion of an overall operating time period.

According to the invention, the time periods in which the signal of the post-catalyst lambda probe lies below or above a threshold value are continuously measured. These time periods are weighted, with respect to the upward transgression of an emission limited value, as a function of the engine speed and load to form two reference time periods in such a way that these reference time periods constitute a measure of the quantity of pollutants emitted in this time period. This makes it possible, from a comparison of the added reference time periods with the overall operating time period of the internal combustion engine, to determine not only for how long the permitted lambda range has not been maintained but also the magnitude of the associated increase in emissions and whether this increase in emissions exceeds a predefined limiting value. If this is the case, a faulty pre-catalyst lambda probe is diagnosed on this basis.

In accordance with an added feature of the invention, the measuring, adding, and diagnosing steps are performed continuously only for as long as the internal combustion engine operates within a predefined engine speed range and a load range.

In accordance with another feature of the invention, a faulty pre-catalyst lambda probe is diagnosed if the signal of the pre-catalyst lambda probe does not oscillate.

In accordance with an additional feature of the invention, a faulty post-catalyst lambda probe is diagnosed if the signal of the post-catalyst lambda probe lies constantly outside an operating range thereof.

In accordance with a further feature of the invention, the first time period, the second time period, and the overall operating time period are measured in real time. It is not necessary, however, to measure the time periods in real time. They can also be detected in units of the oscillation period of the pre-catalyst lambda probe.

In accordance with again an added feature of the invention, the measuring step comprises measuring the first time period, the second time period, and the overall operating time period in units defined by an oscillation period of the signal of the pre-catalyst lambda probe.

In accordance with again another feature of the invention: a difference is formed between the first time period and the second time period in each oscillation period of the signal of the pre-catalyst lambda probe; the difference is weighted in dependence on a sign thereof to form the reference time period; absolute values of the reference time periods of all the oscillation periods are summed; and the summed absolute values are compared with the overall operating time period.

In accordance with again a further feature of the invention, the upper threshold value is defined with a first value for a start and a second value for an end of the upward transgression, and the lower threshold value is defined with a first value for a start and a second value for an end of the downward transgression.

In accordance with yet a further feature of the invention, all of the threshold values are defined in dependence of an engine speed and load.

In one advantageous embodiment of the method, therefore, in each oscillation period of the pre-catalyst lambda probe signal the first time period in which the post-catalyst lambda probe signal exceeds a predefined threshold is subtracted from the second time period in which the post-catalyst lambda probe signal drops below a predefined threshold. Depending on its sign, this difference is, as described, weighted with respect to the upper transgression of a permitted emission of pollutants, as a function of the engine speed and load to form a reference time period. It is then specified in units of the oscillation period. The difference between reference time periods which is obtained in this way is compared with the overall operating time period which is also determined in units of the oscillation period. If the difference between reference time periods exceeds a predefined portion of the overall operating time period, a faulty pre-catalyst lambda probe is diagnosed.

In accordance with a concomitant feature of the invention, the predefined rotational speed and load range is defined in a test cycle. In other words, the process may be carried out only if the engine speed/load conditions, such as are typical for a test cycle which is legally prescribed for determining the emission of pollutants, are present, since these test cycles comprise an engine speed/load range which is characteristic of normal operation. Furthermore, the factors for the weighting of the time periods are advantageously acquired from such test cycles.

The novel method makes it possible to determine how long the permitted lambda range has been departed from during a lambda-controlled catalytic emission treatment, and which increase in emissions is associated with it, and whether a predefined emission limiting value is exceeded. It is not restricted to pre-catalyst lambda probes with two step action but may also be used with linear lambda probes. The method according to the invention is thus an essential prerequisite for the onboard diagnosis of an emission control system.

Other features which are considered as characteristic for the invention are set forth in the appended claims.

Although the invention is illustrated and described herein as embodied in a method for monitoring the emission control system of a spark ignition internal combustion engine, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENT

Figure 1:
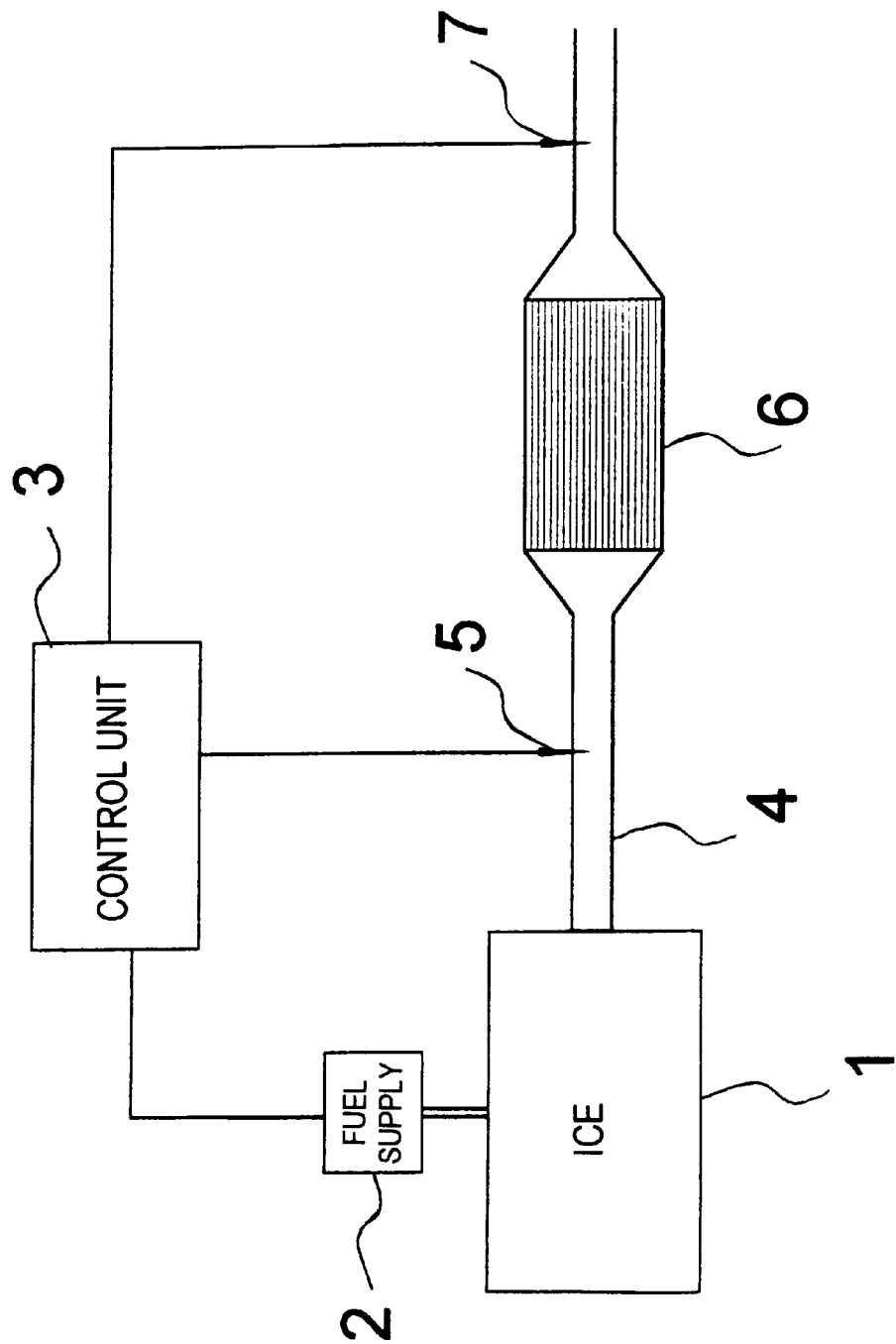
FIG. 1 is a schematic block diagram of an internal combustion engine for carrying out the method according to the invention.

Referring now to the figures of the drawing in detail and first, particularly, to FIG. 1 thereof, there is seen an internal combustion engine 1 with a fuel supply system 2 and a control unit 3. The fuel supply system 2 is actuated by the control unit 3 via lines which are not designated in more detail, and it performs the distribution of fuel to the internal combustion engine 1. In its exhaust tract 4 there is a lambda-controlled catalytic converter 6. To perform the lambda control, a pre-catalyst lambda probe 5 is provided upstream of the catalytic converter 6 and a post-catalyst lambda probe 7 for measuring the lambda value is provided downstream of the catalytic converter. The terms "upstream" and "downstream" are defined relative to the exhaust gas flow direction, i.e. from the internal combustion engine 1, to the catalytic converter 6 and to the exhaust pipe. The two lambda probes supply signals representing their measured values to the control unit 3 via appropriate signal lines. The values of further sensors, in particular the engine speed, the load, the temperature of the catalytic converter etc. are also fed to the control unit 3. Using these values, the control unit 3 controls the operation of the internal combustion engine 1.

When the internal combustion engine 1 is operating, the control of the catalytic emission treatment in the exhaust tract 4 is carried out using the catalytic converter 6 as follows: the supply of fuel in the fuel supply system 2 is controlled in such a way that the signal of the pre-catalyst lambda probe 5 carries out an oscillation about $\lambda=1$. In a normal, fully functional lambda probe, a voltage level of 450 mV corresponds to the value $\lambda=1$. The signal of the pre-catalyst lambda probe 5 oscillates about this value, with the result that the catalytic converter 6 is, on average, fed emissions with the value $\lambda=1$. The post-catalyst lambda probe 7 senses the lambda value in the treated emissions downstream of the catalytic converter 6. Its measured value is used by the control unit 3 to carry out a master control. That is to say the measured value of the post-catalyst lambda probe 7 is used for fine adjustment of the value about which the signal of the pre-catalyst lambda probe 5 oscillates. By means of this master control using the post-catalyst lambda probe 7, a long-term drift of the pre-catalyst lambda probe 5 can be compensated for. If the signal level of the pre-catalyst lambda probe 5 which corresponds to the value $\lambda=1$ shifts, this does not lead to a worsening of the emission treatment in the catalytic converter 6, since the master control using the post-catalyst lambda probe 7 senses this shift and causes the control unit 3 to compensate for it.

Figure 2:
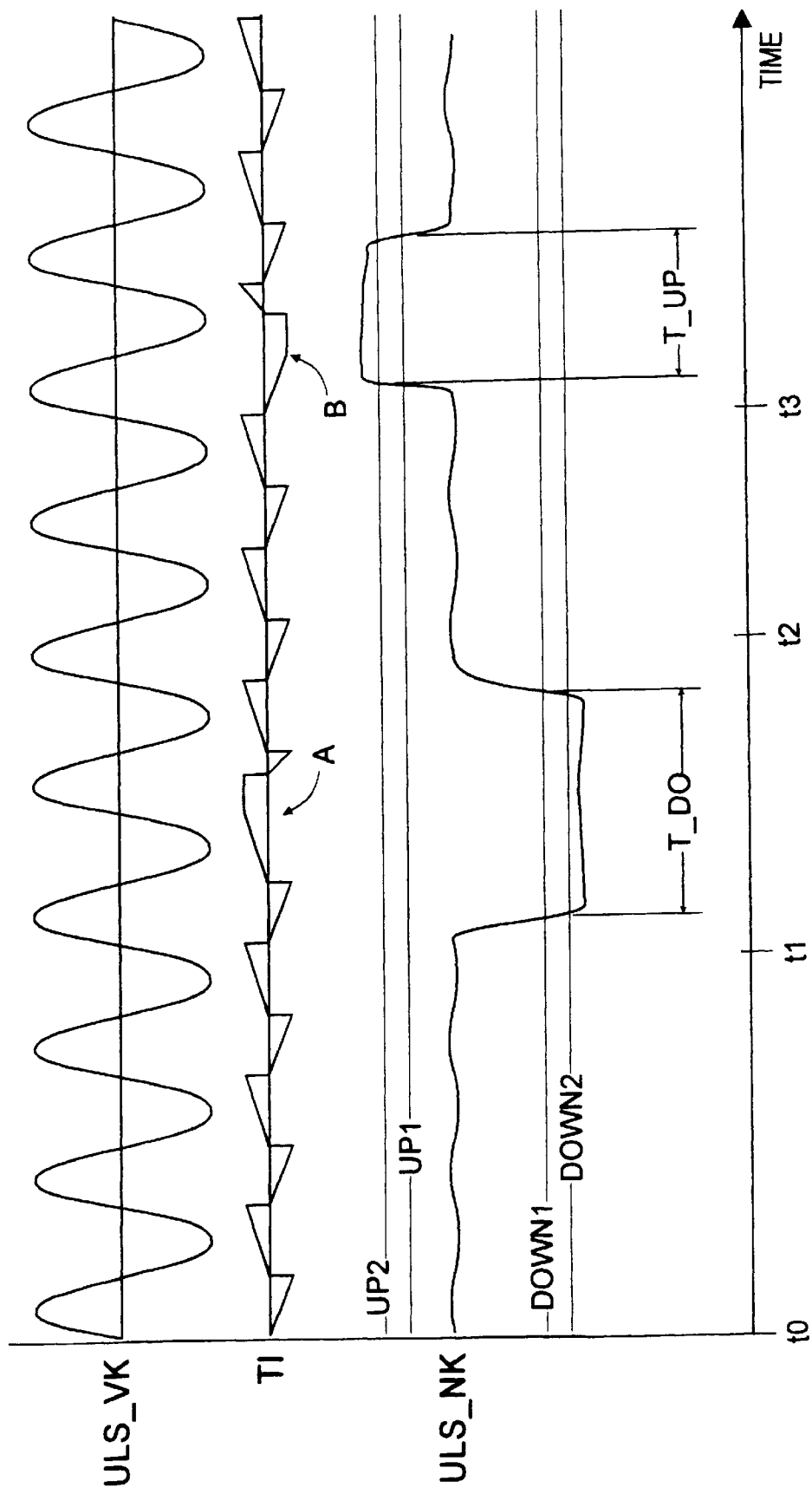
FIG. 2 is a timing diagram showing the time profile of a pre-catalyst lambda probe signal, of a post-catalyst lambda probe signal, and of a fuel supply control signal.

Referring now to FIG. 2, there are shown diagrams with the time signal profiles of the pre-catalyst lambda probe 5, the post-catalyst lambda probe 7 and a fuel supply control signal for the fuel supply system 2. The curve ULS_VK shows the signal profile of the pre-catalyst lambda probe 5, the curve TI shows the time profile of a fuel supply control signal for the fuel supply system 2, and the curve ULS_NK shows the time profile of the signal of the post-catalyst lambda probe 7.

The oscillation of the signal of the pre-catalyst lambda probe 5 about the value for $\lambda=1$ can be clearly seen on the signal profile ULS_VK. High values, that is to say all the parts of the curve above the center line, correspond to a rich mixture in the internal combustion engine 1 and low values correspond to a lean mixture in the internal combustion engine 1. The oscillation of the signal ULS_VK has its origin in the fuel supply control signal TI. If the signal ULS_VK of the pre-catalyst lambda probe 5 oscillates in the lean direction, i.e. the signal drops, more fuel is apportioned to the internal combustion engine 1 and the fuel supply control signal TI increases. The result of this is that the signal ULS_VK changes in the rich direction, i.e. in the direction of higher signal levels. If the value for $\lambda=1$ is reached, the fuel supply control signal TI is returned to the normal value and the saw-toothed-like rise is terminated. The signal ULS_VK of the pre-catalyst lambda probe 5 oscillates in the rich direction, after which the fuel supply control signal TI reduces the apportioning of fuel, i.e. the signal drops. This takes place until the signal ULS_VK passes through the value for $\lambda=1$ again and begins to oscillate in the lean direction. Then, the signal TI is returned again to the normal value and the next rise begins.

The signal ULS_NK of the post-catalyst lambda probe 7 is used for the master control of the pre-catalyst lambda probe signal. The post-catalyst lambda probe 7 measures the lambda value in the treated emissions after the catalytic converter 6. The oscillation about the value $\lambda=1$, which takes place upstream of the catalytic converter 6, is highly damped by the catalytic treatment. The signal ULS_NK carries out only a small oscillation about a fixed central value, as can be seen between the times t0 and t1. This central value corresponds to emissions which have been treated in an optimum way. Such a phase, in which ULS_NK carries out a small oscillation about a fixed central value, the pre-catalyst lambda probe signal ULS_VK carries out an oscillation about $\lambda=1$ and the fuel supply control signal TI carries out an enriching and leaning process of the fuel supply in phase with ULS_VK, can be clearly seen in FIG. 2 between the times t0 and t1.

Between the times t1 and t2, the signal ULS_NK of the post-catalyst lambda probe drops below a predefined threshold DOWN2, although the signal ULS_VK oscillates about the voltage level for $\lambda=1$ without changing. However, the reduced signal ULS_NK shows that the catalytic conversion is not proceeding in an optimum way, in this case the mixture is too lean. The master control in the control unit 3 attempts to compensate for this by prolonging the phases of enrichment of the fuel supply control signal TI. The arrow with reference symbol A indicates such a prolonging process. This prolonged enrichment phase occurs at the expense of the following leaning phase. If the signal ULS_K of the post-catalyst lambda probe 7 returns to the normal range, normal fuel supply takes place again, and the fuel supply control signal TI has the profile as between the times t0 and t1.

In an analogous fashion, when the signal ULS_NK rises above a predefined threshold value, the mixture is made leaner in that the fuel supply control signal in the leaning phases is prolonged. Such a prolonging process is defined with the arrow with the reference symbol B after the time t3.

The checking of the emission control system then takes place as follows:

The time period in which the signal of the post-catalyst lambda probe lies below a predefined threshold value is measured. This time period is indicated by T_DO in FIG. 2. In this time period T_DO, the signal ULS_NK lies below the threshold DOWN2. If ULS_NK rises above DOWN1, this constitutes the end of the time period T_DO. In an analogous fashion, the time period T_UP in which the signal ULS_NK lies above a threshold UP1 or UP2 is measured. In these time periods T_DO and T_UP the catalytic emission treatment does not take place in an optimum way and the internal combustion engine emits increased quantities of pollutants.

In order to acquire a measure of the emitted quantity of pollutants, the time periods T_DO and T_UP are weighted as a function of the engine speed and load to form two reference time periods. This weighting is carried out with respect to the upward transgression of a permitted level of emission of pollutants. Depending on the engine speed or load, a different quantity of pollutants is emitted in a time period. The weighting of the time periods T_DO and T_UP as a function of the engine speed and load to form two reference time periods takes into account this different level of emission of pollutants. The reference time periods are, of course, determined for all the time periods in which the signal ULS_NK lies below or above the predefined threshold values, and added. In a preferred embodiment, the threshold values UP2 and UP1 and DOWN2 and DOWN1 are dependent on the engine speed and load.

The two reference time periods are added to form a total reference time period and a fault is diagnosed in the pre-catalyst lambda probe 5 if this total reference time period exceeds a predefined portion of the overall operating time period which has also been measured. If the operation of the internal combustion engine is terminated in the meantime or if it proceeds outside the predefined engine speed/load ranges, the current totals are stored and the summing is continued until the internal combustion engine is operated in this engine speed/load range again.

Owing to the weighting of the time periods to form reference time periods, the upward transgression means that a permitted limiting value for the emission of pollutants has been exceeded. It is thus possible to determine for how long the permitted lambda range has not been maintained and how large the associated increase in emissions is, and in particular whether the increase in emissions has taken place beyond a permitted limit.

According to a second embodiment of the method according to the invention, the first time period in which the signal ULS_NK lies below an engine speed-dependent and load-dependent threshold value is, in turn, determined and subtracted from the second time period in which the signal ULS_NK lies above an engine speed-dependent and load-dependent threshold value. The difference is weighted as a function of its sign to form a reference time period. The dependence signifies that a positive difference between the first and second time periods is weighted with a different factor than a negative difference. In each case, the weighting factors are load-dependent and engine speed-dependent, in order to obtain a measure of the emitted quantity of pollutants from the difference. The absolute values of the reference time periods of all the oscillation periods of the signal ULS_VK are summed and used for comparison with the overall operating time period which has also been measured. A faulty pre-catalyst lambda probe is, again, diagnosed if the summed absolute values of the reference time periods exceed a predefined portion of the overall operating time period. In this exemplary embodiment, time is measured in units of the oscillation periods of the pre-catalyst lambda probe signal ULS_VK.

A defective catalytic converter which no longer performs adequate catalytic conversion has the result that the signal of the post-catalyst lambda probe carries out the same oscillation as the signal of the pre-catalyst lambda probe, and in doing so alternately overshoots the upper threshold value and undershoots the lower threshold value. The design of the second exemplary embodiment has the advantage that, owing to the subtraction, a defective catalytic converter does not lead to the incorrect diagnosis of a faulty lambda probe in such a case.

The objective of the method is, by continuously monitoring the emission treatment system, to diagnose a fault in a pre-catalyst lambda probe if a predefined emission limiting value is exceeded. Emission limiting values are usually defined over test cycles. In these test cycles, only a limited engine speed/load range is passed through. Weighting factors, such as are necessary to form the reference time periods, are not available for other engine speed/load ranges. For this reason, the method according to the invention is carried out only in those engine speed/load ranges which correspond to engine speed/load ranges such as are typical for the test cycles. If an engine speed or load occurs outside these ranges, first and second time periods of the downward or upward transgression of predefined threshold values are not measured or added. If the limited engine speed/load ranges which are described above occur, these time periods are determined, weighted as a function of engine speed and load to form reference time periods and the total reference time period is continuously added and is then used for comparison with the overall operating time period.

A faulty pre-catalyst lambda probe 5 is also diagnosed if the oscillation of the pre-catalyst lambda probe signal ULS_VK does not occur.

A faulty post-catalyst lambda probe 7 is diagnosed if the signal ULS_NK permanently lies outside the operating range.

I claim:

1. A method for monitoring an emission control system of a spark ignition internal combustion engine, wherein the emission control system includes a lambda-controlled catalytic converter subjected to an exhaust gas flow, a pre-catalyst lambda probe disposed upstream of the catalytic converter in an exhaust gas flow direction, and a post-catalyst lambda probe disposed downstream of the catalytic converter, the method which comprises:

controlling a fuel supply system of an internal combustion engine by master control of the post-catalyst lambda probe such that a signal of the pre-catalyst lambda-probe oscillates about a value $\lambda=1$;

measuring a first time period in which a signal of the post-catalyst lambda probe lies below a predefined lower threshold value and a second time period in which the signal of the post-catalyst lambda probe lies above a predefined upper threshold value, and weighting the first and second time periods with respect to an upward transgression of a permitted emission of pollutants to form two reference time periods in dependence on rotational speed and a load;

adding the reference time periods to form a total reference time period; and diagnosing a fault in the pre-catalyst lambda probe if the total reference time period exceeds a predefined portion of an overall operating time period.

2. The method according to claim 1, wherein the measuring, adding, and diagnosing steps are performed continuously only for as long as the internal combustion engine operates within a predefined engine speed range and a load range.

3. The method according to claim 1, which comprises diagnosing a faulty pre-catalyst lambda probe if the signal of the pre-catalyst lambda probe does not oscillate.

4. The method according to claim 1, which comprises diagnosing a faulty post-catalyst lambda probe if the signal of the post-catalyst lambda probe lies constantly outside an operating range thereof.

5. The method according to claim 1, wherein the measuring step comprises measuring the first time period, the second time period, and the overall operating time period in real time.

6. The method according to claim 1, wherein the measuring step comprises measuring the first time period, the second time period, and the overall operating time period in units defined by an oscillation period of the signal of the pre-catalyst lambda probe.

7. The method according to claim 1, wherein:

the measuring step comprises forming a difference between the first time period and the second time period in each oscillation period of the signal of the pre-catalyst lambda probe;

weighting the difference in dependence on a sign thereof to form the reference time period;

the adding step comprises summing absolute values of the reference time periods of all the oscillation periods; and the diagnosing step comprises comparing the summed absolute values with the overall operating time period.

8. The method according to claim 1, which comprises, in the measuring step, defining the upper threshold value with a first value for a start and a second value for an end of the upward transgression, and defining the lower threshold value with a first value for a start and a second value for an end of the downward transgression.

9. The method according to claim 1, wherein the threshold values are defined in dependence of an engine speed and load.

10. The method according to claim 1, which comprises defining the predefined rotational speed and load range in a predefined test cycle.

* * * * *